US 8,565,894 B2

(12) United States Patent
Vetter et al.

(10) Patent No.: US 8,565,894 B2
(45) Date of Patent: Oct. 22, 2013

(54) THREE-DIMENSIONAL SYSTEM OF ELECTRODE LEADS

(75) Inventors: Rio J. Vetter, Ypsilanti, MI (US); Daryl R. Kipke, Dexter, MI (US); Jamille F. Hetke, Brooklyn, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 470 days.

(21) Appl. No.: 12/253,803

(22) Filed: Oct. 17, 2008

(65) Prior Publication Data
US 2009/0118806 A1 May 7, 2009

Related U.S. Application Data

(60) Provisional application No. 60/980,657, filed on Oct. 17, 2007.

(51) Int. Cl.
*A61N 1/00* (2006.01)
(52) U.S. Cl.
USPC .......................................... 607/116
(58) Field of Classification Search
USPC .......................................... 607/116
See application file for complete search history.

(56) References Cited

U.S. PATENT DOCUMENTS

| 3,847,687 A | 11/1974 | Davidsohn et al. |
| 3,921,916 A | 11/1975 | Bassous |
| 4,141,365 A | 2/1979 | Fischell et al. |
| 4,166,469 A | 9/1979 | Littleford |
| 4,306,562 A | 12/1981 | Osborne |
| 4,455,192 A | 6/1984 | Tamai |
| 4,461,304 A | 7/1984 | Kuperstein |
| 4,465,482 A | 8/1984 | Tittel |
| 4,762,135 A | 8/1988 | van der Puije |
| 4,886,065 A | 12/1989 | Collins |

(Continued)

FOREIGN PATENT DOCUMENTS

| WO | PCT/CA00/00942 | 2/2001 |
| WO | 0241666 | 5/2002 |

(Continued)

OTHER PUBLICATIONS

Seymour, John P., Kipke, Daryl R. "Neural probe design for reduced tissue encapsulation in CNS" 28 (2007) 3594-3607, Apr. 5, 2007.
Seymour, John P., Elkasabi, Yaseen M., Chen, Hsien-Yeh, Lahann, Joerg, Kipke, Daryl R., "The insulation performance of reactive parylene films in implantable electronic devices" Biomaterials 30 (2009) 6158-6167, Aug. 22, 2009.

(Continued)

*Primary Examiner* — Christopher D Koharski
*Assistant Examiner* — Philip Edwards
(74) *Attorney, Agent, or Firm* — Michael F. Scalise

(57) ABSTRACT

The electrode lead system of a preferred embodiment includes a series of first electrical subsystems; a guiding element that positions the series of first electrical subsystems in a three dimensional arrangement within body tissue; a second electrical subsystem; and at least one connector that couples the first electrical subsystems to the second electrical subsystem. The electrode lead system of another preferred embodiment includes a series of electrode arrays; a guide tube that facilitates implantation of electrode arrays within body tissue and temporarily contains the series of electrode arrays; and a guiding element that provides a bias on the series of electrode arrays such that (a) when contained by the guide tube, the first electrical subsystems maintain a substantially singular path within body tissue, and (b) when not contained by the guide tube, the first electrical subsystems diverge along more than one path into a three dimensional arrangement within body tissue.

41 Claims, 1 Drawing Sheet

(56) References Cited

U.S. PATENT DOCUMENTS

| | | |
|---|---|---|
| 4,904,237 A | 2/1990 | Janese |
| 5,108,819 A | 4/1992 | Heller et al. |
| 5,180,376 A | 1/1993 | Fischell |
| 5,207,709 A | 5/1993 | Picha |
| 5,215,088 A | 6/1993 | Normann et al. |
| 5,308,442 A | 5/1994 | Taub et al. |
| 5,322,064 A * | 6/1994 | Lundquist .................... 600/381 |
| 5,385,635 A | 1/1995 | O'Neill |
| 5,390,671 A | 2/1995 | Lord |
| 5,409,469 A | 4/1995 | Schaerf |
| 5,496,360 A | 3/1996 | Hoffmann et al. |
| 5,515,848 A | 5/1996 | Corbett, III et al. |
| 5,524,338 A | 6/1996 | Martyniuk et al. |
| 5,573,520 A | 11/1996 | Schwartz et al. |
| 5,585,827 A | 12/1996 | Murakami |
| 5,588,597 A | 12/1996 | Reinecke et al. |
| 5,720,099 A | 2/1998 | Parker et al. |
| 5,744,958 A | 4/1998 | Werne |
| 5,800,535 A | 9/1998 | Howard, III |
| 5,843,150 A | 12/1998 | Dreessen et al. |
| 5,927,277 A | 7/1999 | Baudino et al. |
| 5,938,694 A * | 8/1999 | Jaraczewski et al. ......... 607/122 |
| 5,975,085 A | 11/1999 | Rise |
| 5,989,445 A | 11/1999 | Wise et al. |
| 5,992,769 A | 11/1999 | Wise et al. |
| 6,006,124 A | 12/1999 | Fischell et al. |
| 6,016,449 A | 1/2000 | Fischell et al. |
| 6,044,304 A | 3/2000 | Baudino |
| 6,132,456 A | 10/2000 | Sommer et al. |
| 6,181,569 B1 | 1/2001 | Chakravorty |
| 6,205,361 B1 | 3/2001 | Kuzma et al. |
| 6,228,111 B1 | 5/2001 | Tormala et al. |
| 6,324,433 B1 | 11/2001 | Errico |
| 6,325,797 B1 * | 12/2001 | Stewart et al. ................... 606/41 |
| 6,374,143 B1 | 4/2002 | Berrang et al. |
| 6,430,443 B1 | 8/2002 | Karell |
| 6,600,231 B2 | 7/2003 | Tominaga |
| 6,618,623 B1 | 9/2003 | Pless et al. |
| 6,829,498 B2 * | 12/2004 | Kipke et al. .................. 600/378 |
| 6,834,200 B2 | 12/2004 | Moxon et al. |
| 6,878,643 B2 | 4/2005 | Krulevitch et al. |
| 7,004,948 B1 | 2/2006 | Pianca et al. |
| 7,006,859 B1 | 2/2006 | Osorio et al. |
| 7,010,356 B2 | 3/2006 | Jog et al. |
| 7,011,680 B2 | 3/2006 | Alt |
| 7,089,059 B1 | 8/2006 | Pless |
| 7,181,288 B1 * | 2/2007 | Rezai et al. ................... 607/116 |
| 7,343,205 B1 | 3/2008 | Pianca et al. |
| 7,548,775 B2 | 6/2009 | Kipke et al. |
| 7,871,707 B2 | 1/2011 | Laude et al. |
| 7,914,842 B1 | 3/2011 | Greenberg et al. |
| 7,941,202 B2 | 5/2011 | Hetke et al. |
| 2001/0049499 A1 | 12/2001 | Lui et al. |
| 2002/0052610 A1 | 5/2002 | Skakoon et al. |
| 2002/0183817 A1 | 12/2002 | Van Venrooij et al. |
| 2002/0198446 A1 | 12/2002 | Hill et al. |
| 2003/0093129 A1 | 5/2003 | Nicolelis et al. |
| 2003/0100823 A1 | 5/2003 | Kipke |
| 2003/0114906 A1 * | 6/2003 | Booker et al. ................. 607/122 |
| 2003/0187461 A1 | 10/2003 | Chin |
| 2004/0006264 A1 | 1/2004 | Mojarradi et al. |
| 2004/0102828 A1 | 5/2004 | Lowry et al. |
| 2004/0106169 A1 | 6/2004 | Evans |
| 2004/0199235 A1 | 10/2004 | Younis |
| 2005/0004627 A1 | 1/2005 | Gibson et al. |
| 2005/0021116 A1 | 1/2005 | He et al. |
| 2005/0021117 A1 | 1/2005 | He et al. |
| 2005/0137647 A1 | 6/2005 | Wallace et al. |
| 2005/0222647 A1 * | 10/2005 | Wahlstrand et al. ............ 607/72 |
| 2006/0122677 A1 * | 6/2006 | Vardiman .................... 607/116 |
| 2006/0173263 A1 | 8/2006 | He et al. |
| 2006/0247749 A1 | 11/2006 | Colvin |
| 2006/0258951 A1 | 11/2006 | Bleich et al. |
| 2006/0276866 A1 | 12/2006 | McCreery |
| 2006/0282014 A1 | 12/2006 | Kipke |
| 2007/0073130 A1 | 3/2007 | Finch et al. |
| 2007/0123765 A1 | 5/2007 | Hetke et al. |
| 2007/0135885 A1 | 6/2007 | Risi |
| 2008/0132970 A1 | 6/2008 | Barolat |
| 2008/0208283 A1 | 8/2008 | Vetter et al. |
| 2008/0255439 A1 | 10/2008 | Tang et al. |
| 2008/0262584 A1 | 10/2008 | Bottomley et al. |
| 2009/0099555 A1 | 4/2009 | Viohl et al. |
| 2009/0102068 A1 | 4/2009 | Pellinen et al. |
| 2009/0132042 A1 | 5/2009 | Hetke et al. |
| 2009/0149934 A1 | 6/2009 | Ameri et al. |
| 2009/0171421 A1 | 7/2009 | Atalar et al. |
| 2009/0187196 A1 | 7/2009 | Vetter et al. |
| 2009/0234426 A1 | 9/2009 | Pellinen et al. |
| 2009/0240314 A1 | 9/2009 | Kong et al. |
| 2009/0248118 A1 | 10/2009 | Bradley et al. |
| 2009/0253977 A1 | 10/2009 | Kipke et al. |
| 2009/0299167 A1 | 12/2009 | Seymour |
| 2009/0312770 A1 | 12/2009 | Kozai et al. |
| 2010/0030298 A1 | 2/2010 | Martens et al. |
| 2010/0145216 A1 | 6/2010 | He et al. |
| 2010/0145422 A1 | 6/2010 | Seymour et al. |
| 2011/0093052 A1 | 4/2011 | Anderson et al. |
| 2011/0154655 A1 | 6/2011 | Hetke et al. |

FOREIGN PATENT DOCUMENTS

| | | |
|---|---|---|
| WO | PCT/EP00/10775 | 5/2002 |
| WO | PCT/US02/16942 | 12/2002 |
| WO | PCT/US2004/035030 | 5/2005 |
| WO | 2006138358 A | 12/2006 |
| WO | 2007042999 A | 4/2007 |
| WO | 2007089738 A | 8/2007 |
| WO | 2008011721 A | 1/2008 |
| WO | 2008038208 A | 4/2008 |
| WO | 2008072125 A | 6/2008 |
| WO | 2008109298 A | 9/2008 |
| WO | 2009052423 A | 4/2009 |
| WO | 2009052425 A | 4/2009 |
| WO | 2010057095 A | 5/2010 |
| WO | 2011/010257 | 1/2011 |
| WO | 2011010257 A | 1/2011 |
| WO | 2011046665 A | 4/2011 |

OTHER PUBLICATIONS

Kaplan, et al., "A Novel Fabrication Method of Capillary Tubes on Quartz for Chemical Analysis Applications" IEEE Proceedings, Micro Electro Mechanical Systems, Jan. 25-28, 1994.

Lin, et al., "Silicon Processed Microneedles" The 7th International Conference on Solid State Sensors and Acutators; Jun. 7-10, 1993.

U.S. Appl. No. 12/986,081, Hetke.

Application No. PCT/IB06/53700, International Search Report mailed Nov. 21, 2008.

Application No. PCT/IB10/53250, International Search Report mailed Oct. 4, 2010.

Application No. PCT/US04/35030, International Search Report mailed Feb. 21, 2005.

Application No. PCT/US06/23139, International Search Report mailed Aug. 2, 2007.

Application No. PCT/US07/02465, International Search Report mailed Feb. 13, 2008.

Application No. PCT/US08/55025, International Search Report and Written Opinion mailed Oct. 27, 2008.

Application No. PCT/US08/80364, International Search Report and Written Opinion mailed Dec. 16, 2008.

Application No. PCT/US08/80366, International Search Report and Written Opinion mailed Dec. 10, 2008.

Application No. PCT/US09/64591, International Search Report and Written Opinion mailed Jul. 21, 2010.

Application No. PCT/US10/44167, International Search Report and Written Opinion mailed Sep. 27, 2010.

Lin et al., "Silicon Processed Microneedles," IEEE J. Micro. Electro. Mech. Sys, vol. 8, No. 1 (1999) 78-84 (7 pages).

* cited by examiner

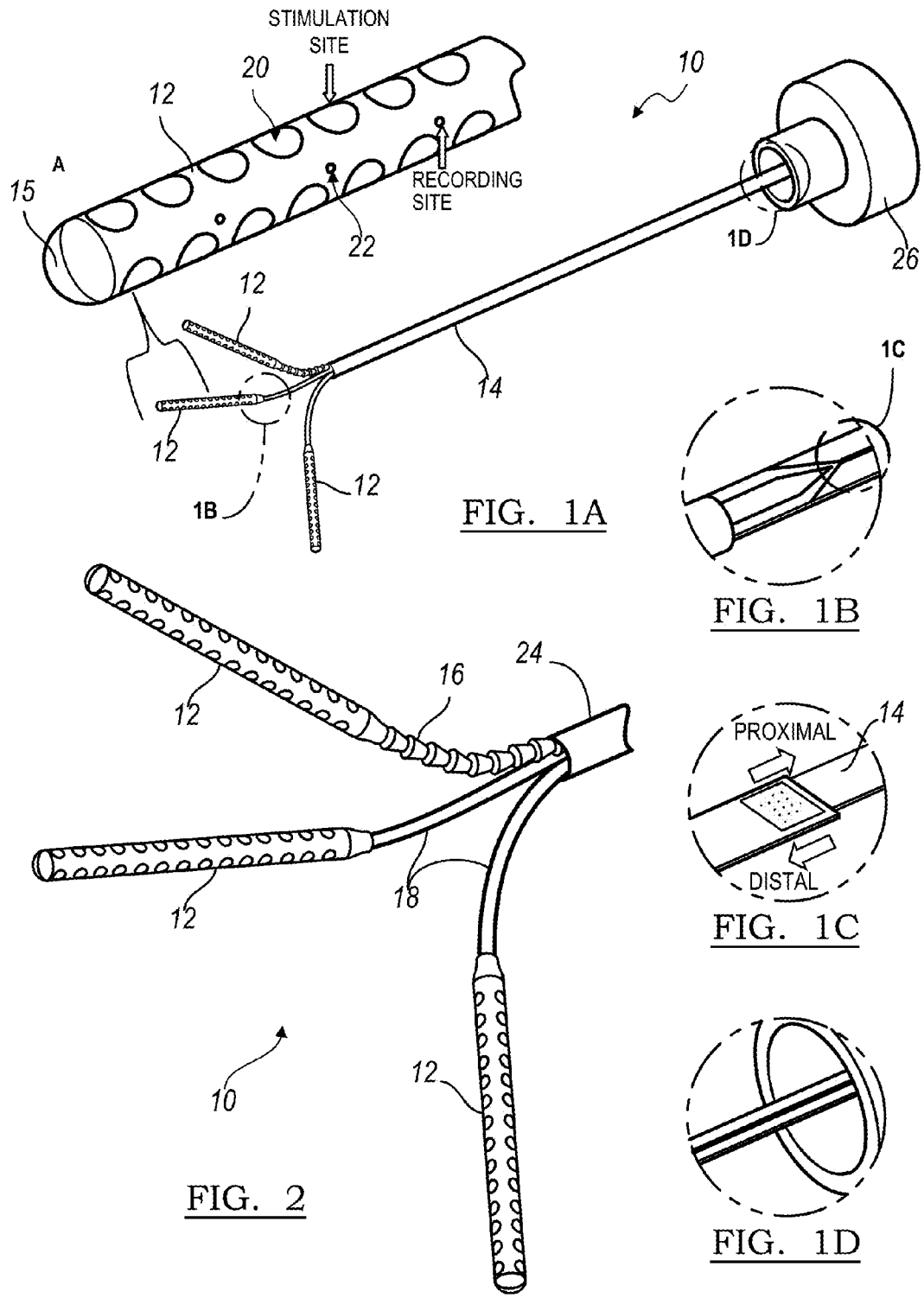

THREE-DIMENSIONAL SYSTEM OF ELECTRODE LEADS

CROSS-REFERENCE TO RELATED APPLICATIONS

This application claims the benefit of U.S. Provisional Application No. 60/980,657 filed 17 Oct. 2007 and entitled "Three-Dimensional System of Electrode Leads", which is hereby incorporated in its entirety by this reference.

This application is related to U.S. Publication Number 2008/0208283 published on 28 Aug. 2008 and entitled "Neural Interface System", which is incorporated in its entirety by this reference.

TECHNICAL FIELD

This invention relates generally to the electrode lead field, and more specifically to an improved system of electrode leads that can interface with tissue in a three-dimensional manner.

BACKGROUND

Chronic Deep Brain Stimulation (DBS) devices—'brain pacemakers'—have emerged in the last decade as a revolutionary new approach to the treatment of neurological and psychiatric disorders. Conventional DBS therapy involves controllable electrical stimulation through a lead having four relatively large electrodes that are implanted in the targeted region of the brain. While conventional DBS therapy is generally safe and effective for reducing cardinal symptoms of the approved diseases, it often has significant behavioral and cognitive side effects and limits on performance. Additionally, the therapeutic effect is highly a function of electrode position with respect to the targeted volume of tissue, and more specifically, a function of which neuronal structures are influenced by the charge being delivered. With conventional electrodes, there are limitations as to how the charge is delivered and stimulation fields are limited as all of the electrode sites involved with stimulation are positioned along a single axis. Thus, there is a need for an improved system of electrode leads to provide fine electrode positioning, selectivity, precise stimulation patterning, and precise lead location. This invention provides such an improved and useful system of electrode leads.

BRIEF DESCRIPTION OF THE FIGURES

FIG. 1 is a schematic drawing of an electrode lead system with a plurality of first electrical subsystems.

FIG. 2 is a schematic drawing of the first and second variation of the guiding element of the electrode lead system of the preferred embodiment.

DESCRIPTION OF THE PREFERRED EMBODIMENTS

The following description of preferred embodiments of the invention is not intended to limit the invention to these embodiments, but rather to enable any person skilled in the art to make and use this invention.

As shown in FIG. 1, the electrode lead system 10 of the preferred embodiments includes a series of first electrical subsystems 12, a guiding element that positions the series of first electrical subsystems 12 in a three dimensional arrangement, a second electrical subsystem, and at least one connector 14 that couples the first electrical subsystems 12 to the second electrical subsystem. The electrode lead system 10 may further include a guide tube 24 and/or a stylet that facilitates the insertion of the series of first electrical subsystems 12, provides structural support to the system during implantation, and/or cooperatives with the guiding element to position the series of first electrical subsystems 12 in a three dimensional arrangement. The system 10 of the preferred embodiment is preferably designed for an implantable electrode lead system for deep brain stimulation, and, more specifically, for an implantable electrode lead system that can interface with deep brain tissue in a three-dimensional manner. The system 10 of the preferred embodiments, however, may be alternatively used in any suitable environment (such as the spinal cord, peripheral nerve, muscle, or any other suitable anatomical location) and for any suitable reason.

1. The Guiding Element

The guiding element of the preferred embodiment functions to position the series of first electrical subsystems 12 in a three dimensional arrangement. The electrode lead system 10 may include one guiding element for every first electrical subsystem 12, such that the ratio of guiding elements to first electrical subsystems 12 is 1:1. Alternatively, the electrode lead system 10 may include one guiding element for every two or more first electrical subsystems 12, such that the ratio of guiding elements to first electrical subsystems 12 is less than 1:1. Additionally, the guiding elements may be coupled to a chamber 26, as shown in FIGS. 1A and 1D, or any other suitable element of the electrode lead system 10 and may include a sharpened end adapted to penetrate the tissue and aid in the insertion of the electrical subsystems and/or guiding elements into the tissue. The guiding element is preferably one of several variations.

In a first variation, as shown in FIG. 2, the guiding element is a maneuverable guiding element 16. In this variation, the maneuverable guiding element 16 is adapted such that a user may maneuver the series of first electrical subsystems 12 into the tissue in a three-dimensional arrangement. In this variation, the maneuverable guiding element 16 is coupled to the first electrical subsystem 12 and includes a system of cables or robotics that are controlled by a user to position the subsystems. The maneuverable guiding element 16 may further include joints or connections, as shown in FIG. 2, such that the maneuverable guiding element 16 is adapted to move and position the subsystems in the tissue. The maneuverable guiding element 16 may also be guidable remotely and/or wirelessly or in any other suitable fashion with any suitable combination of guiding elements 16.

In a second variation, as also shown in FIG. 2, the guiding element is a biased guiding element 18. In this variation, the biased guiding element 18 is biased to move into a three-dimensional arrangement such that it will move into that arrangement as it are inserted into the tissue. In this variation, the biased guiding element 18 is preferably made from a material with shape memory or high elasticity. The biased guiding element 18 is preferably used with the version of the electrode lead system 10 that includes a guide tube 24. When the first electrical subsystems 12 and biased guiding element 18 are in the guide tube 24, they are compact and generally straight. When the guide tube 24 is pulled off of the first electrical subsystems 12, or the first electrical subsystems 12 are pushed past the end of the guide tube 24, the biased guiding element 18 will begin to return to its original shape or change shape and move the first electrical subsystems 12 into a three-dimensional arrangement. Preferably, as the first electrical subsystems are pushed further into the tissue, the biased guiding element 18 will position them further away from one another into a three-dimensional arrangement, i.e. the depth of the subsystems dictates their location and three-dimensional spatial distance from one another. The biased guiding element 18 may alternatively be biased in any other suitable fashion in any other suitable three-dimensional arrangement. The material of the biased guiding element 18 is preferably an elastic material such as metal or plastic, or a shape memory material such as nitinol. The material may alternatively be made from any suitable material. The shape memory material may change shape due to temperature, electrical stimulus, or any other suitable mechanism. Prior to use, the first electrical subsystems 12 and biased guiding element 18 are preferably stored or prepared for use in a package, such as the guide tube 24, in their compact state, to facilitate transport and use, but may alternatively be stored or prepared for use in any other suitable fashion.

As previously mentioned, the electrode lead system 10 of the preferred embodiments may include a guide tube 24 and/or a stylet. The guide tube 24 functions to facilitate the insertion of the series of first electrical subsystems 12, functions to provide structural support to the system during implantation, and/or cooperatively functions with the guiding element to position the series of first electrical subsystems 12 in a three dimensional arrangement. The guide tube 24 may be further adapted to store the series of first electrical subsystems 12 and the biased guiding element 18 in their compact state, to facilitate transport and use. The guide tube 24 and/or stylet is preferably made of a rigid material, which can be inserted into tissue or other substances without buckling and can maintain a generally straight trajectory through the tissue. The material may be uniformly rigid, or rigid only in a particular direction (such as the axial direction). The material is preferably plastic (such as a medical grade plastic) or metallic (such as titanium), but may alternatively be any suitable material such as metal or a combination of materials. The guide tube 24 and/or stylet may further include a sharpened end adapted to penetrate the tissue and aid in the insertion of the guide tube 24 into the tissue, and may also include alignment and or fixation features to facilitate positioning and stabilizing the series of first electrical subsystems 12 in the tissue, particularly during removal of the guide tube.

Although the guiding element is preferably one of these two variations, the electrode lead system 10 may be adapted to be introduced into the tissue three-dimensionally in any suitable manner with any suitable combination of devices.

2. Series of First Electrical Subsystems

The first electrical subsystems 12 of the preferred embodiments function to interface with the tissue, or any other suitable substance, within which they have been implanted. The first electrical subsystems 12 may include multiple different electrical subsystems or a plurality of the same subsystems. The first electrical subsystem is preferably at least one of several variations or any combination thereof. In a first variation, the first electrical subsystem 12 is a multi-banded cylindrical electrode with a linear arrangement of four equally spaced cylindrical electrodes, which can be used in monopolar or bipolar modes to deliver electrical stimulation to the surrounding tissue. The electrodes can deliver approximately spherical potential fields from separate locations along a cylindrical carrier.

In a second variation, as shown in FIG. 1, the first electrical subsystem 12 is a neural interface electrode array. The electrode array preferably has a plurality of electrode sites, and more preferably has more than four electrode sites. The neural interface electrode array is adapted to provide dynamic tunable electrical stimulation ranging from stimulation with macroscale specificity to microscale directional patterning. The electrode array is preferably adapted to optimally sample (record) and/or selectively activate (stimulate) neural populations. The plurality of electrode sites are preferably tuned for recording, stimulation, any other suitable function, or any combination thereof. Additionally, at least two electrode sites may be grouped to form a larger composite site that enables tuning the neural interface region for recording and/or stimulation. This grouping of sites can be through intrinsic connection of the site traces, or it can be through external connections for 'on the fly' tuning. The electrode array may further include fluidic channels providing the capability to deliver therapeutic drugs, drugs to inhibit biologic response to the implant, or any other suitable fluid.

For stimulation, a larger composite site increases the effective site area to allow increased charge injection while maintaining safe electrochemical and biological limits. This will enable, for example, precise current steering to selectively stimulate neural structures. For recording, a composite site can be used to change the recording selectivity of the device to emphasize, for example, field potential recording over single-unit recordings. The composite sites can have diverse shapes that are driven by desired requirements of the neural interface. For example, a composite site may be a vertical strip along the array or a horizontal band. It may also tie together opposing strips to form a contiguous band. Composite sites can be used to establish one or more tunable neural interface region for the device. Multiple neural interface regions can be overlapping or non-overlapping.

The ability to combine microelectrode and macroelectrode sites on a single device allows for sites to be used in a customized mode of operation. The positions of the sites selected for stimulation can be adjusted as needed to optimally interface with the neural region of interest. This allows for sites to be configured to create an optimized arrangement of anode and cathode configurations. Additionally, sites can be used on an individual basis or as a group to effectively form a single macroelectrode comprised of a plurality of microelectrodes. This provides an additional degree of freedom when tuning the stimulation parameters in order to optimally interface with the targeted neural region.

The neural interface electrode array is preferably made from a thin-film polymer substrate such that there is high density of electrode sites at a first end of the array (the distal end) and bonding regions at a second end of the array (the proximal end). The polymer substrate is preferably parylene or some combination of parylene and inorganic dielectrics, but may alternatively be made out of any suitable material. The distal end of the array is preferably coupled to a carrier to provide structural support. Additionally, the distal end will be in direct contact with the tissue and so will preferably be made from suitable materials for both biocompatibility and dielectrics.

The neural interface electrode array is preferably comprised of conductive interconnects disposed between layers of dielectrics that insulate the interconnects on top and bottom sides. At least some interconnects preferably terminate with electrode sites on the distal end and/or with bond pads for electrical connection to external instrumentation and/or hybrid chips on the proximal end. The electrode sites are preferably patterned directly onto the polymer substrate. The precision, consistency, and reproducibility of the electrode sites on the microelectrode array result in predictable electrical and spatial characteristics. These characteristics enable the sites to be grouped in a manner that enables precise, predictable, and selective tuning of neural interface regions. The electrode sites are preferably metal such as iridium, platinum, gold, but may alternatively be any other suitable material. The conductive leads or traces are preferably metal or polysilicon, but may alternatively be any other suitable material. Polyimide, parylene, inorganic dielectrics, or a composite stack of silicon dioxide and silicon nitride is preferably used for the dielectrics however, any other suitable materials may alternatively be used.

In one specific variation of the neural interface electrode array, as shown in FIG. 1, the electrode array preferably includes sixty-four stimulation electrodes 20 and thirty-two recording electrodes 22 positioned around and along a carrier. Each stimulation site 20 has a surface area of preferably 0.196 mm$^2$ (diameter=500 μm), but may alternatively have any suitable surface area. Each recording site 22 has a surface area of preferably 0.00196 mm$^2$ (diameter=50 μm), but may alternatively have any suitable surface area. The stimulation sites 20 are preferably positioned such that four sites will be equally spaced around the circumference of a carrier (center-to-center spacing" 750 μm). Sites will also be preferably spaced at 750 μm in the axial direction (center-to-center) and positioned at sixteen successive locations. Between each row of stimulations sites 20, two recording sites 22 will preferably be positioned on opposite sides of the cylinder. The positions of each recording site pair 22 will preferably shift ninety degrees between successive depths. Alternatively, there may be any suitable number of stimulation sites 20 and recording sites 22, and the stimulation sites 20 and recording sites 22 may alternatively be positioned in any other suitable arrangement.

The first electrical subsystem 40 may be adapted for long term implantation as in the first two variations, or alternatively may be adapted for short-term intraoperative use as in the following third variation. In the third variation, the first electrical subsystem 12 is a mapping electrode system, which is adapted to perform clinical deep brain electrophysiological mapping for use in neurosurgical applications. More specifically, the mapping electrode system is preferably adapted to perform simultaneous multichannel neural recording from precisely known locations along the deep microelectrode track. The mapping electrode may further have extended functionality such as multichannel recording and/or stimulation or fluid delivery. The mapping electrode system is preferably a planar electrode array disposed on an insulated metal wire. The metal wire is preferably made from a metal such as tungsten, stainless steel, platinum-iridium, or any other suitable metal. The electrode array preferably includes multiple recording sites and more preferably includes twenty-four recording sites (twelve on each side) spaced to provide neural recordings. Although the first electrical subsystem 12 is preferably one of these several variations, the first electrical subsystem 12 may be any suitable element or combination of elements to perform the desired functions.

3. The Second Electrical Subsystem and the Connector

The second electrical subsystem of the preferred embodiments functions to operate with the first electrical subsystem 12. The second electrical subsystem may include multiple different electrical subsystems or a series of the same subsystems. The second electrical subsystem is preferably at least one of several variations or any combination thereof. The second electrical subsystem is a suitable electronic subsystem to operate with an implantable neural interface. The second electrical subsystem may be a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable pulse generator, an implantable rechargeable battery, integrated electronics for either real-time signal processing of the input (recorded) or output (stimulation) signals, integrated electronics for control of the fluidic components, any other suitable electrical subsystem, or any combination thereof. Although the second electrical subsystem is preferably one of these several subsystems, the second electrical subsystem may be any suitable element or combination of elements to operate any suitable first electrical subsystem(s) 12.

The connector 14 of the preferred embodiments functions to couple the first electrical subsystems 12 to the second electrical, subsystem. The connector 14 is preferably one of several variations. As shown in FIG. 1, the connector 14 is preferably a flexible ribbon cable. The ribbon cable is preferably polymer ribbon cable, but may alternatively be any other suitable ribbon cable. The ribbon cable may be encased in silicone or any other suitable material. In some situations, the electrical subsystem may have multiple ribbon cables. Preferably, multiple ribbon cables would be physically attached along their entire length, using a suitable adhesive such as medical grade adhesive or any other suitable connection mechanism. The cable is preferably connected to the electrical subsystems through ball bonds, or any other suitable connection mechanisms. The connector 14 may alternatively be seamlessly manufactured with the first and or second electrical subsystem. The connector 14 may further include fluidic channels adapted to deliver therapeutic drugs, drugs to inhibit biologic response to the implant, or any other suitable fluid. The connector 14 may alternatively be any suitable element to couple the first electrical subsystems 12 to the second electrical subsystem, such as wires, conductive interconnects, etc.

4. Variations of the Preferred Embodiments

As shown in FIG. 1A, the electrode lead system 10 of the preferred embodiment may further include a carrier 15. The carrier functions to shuttle the first electrical subsystem 12 and the connector 14 into tissue or other substances. In some variations, the first electrical subsystem 12 is attached to the carrier, such that the carrier 15 functions to provide structural support. The shape of the carrier is preferably tubular with about a 1-mm diameter, but may alternatively be any suitable shape of any suitable diameter for the desired functions. The carrier may include a sharpened end adapted to penetrate the tissue and aid in the insertion of the carrier and electrical subsystems into the tissue. The carrier may further extend the functionality of the system by providing fluidic channels through which therapeutic drugs, drugs to inhibit biologic response to the implant, or any other suitable fluid may be transmitted. This provides for the precise delivery of specific pharmaceutical compounds to localized regions of the body, such as the nervous system, and could facilitate, for example, intraoperative mapping procedures or long-term therapeutic implant devices. The fluidic channels may also provide a location through which a stiffener or stylet may be inserted to aid with implantation. Alternatively, the carrier may further include a separate lumen through which the stiffener or stylet may be inserted.

The carrier is preferably one of several variations. In a first variation, the carrier is a polymeric carrier. The carrier is preferably made of polyimide or silicon, but may be alternatively made from any other suitable material. The carrier is preferably flexible, but may alternatively be rigid or semi rigid. In a second variation, the carrier is resorbable carrier, which is resorbed into tissue after a period of time. If the carrier is supporting a first electrical subsystem 12, upon resorption, the subsystem will be left to float freely in the brain or other suitable tissue or material. The resorbable carrier is preferably made of implantable medical fabric woven or knitted from a bioresorbable polymer. The bioresorbable polymer is preferably polyglycolide or polylactide, but may alternatively be made from any suitable bioresorbable material. Although the carrier is preferably one of these two variations, the carrier may be any suitable element to shuttle the first electrical subsystem 12 and the connector 14 into tissue or other substances and provide structural support.

The electrode lead system 10 of the preferred embodiment may further include a stylet. The stylet of the preferred embodiments functions to penetrate the tissue or other material, functions to provide structural support to the system during implantation, and/or cooperatively functions with the guiding element to position the series of first electrical subsystems 12 in a three dimensional arrangement. The stylet is preferably inserted into a lumen of a carrier, but may alternatively be located and inserted into any suitable component of the system in any suitable manner. The stylet may include a sharpened end adapted to penetrate the tissue and aid in the insertion of the stylet, the carrier, and/or the electrical subsystems into the tissue. The stylet is preferably removed from the tissue following the placement of an electrical subsystem, but may alternatively be adapted to remain in the tissue while still allowing the implanted first electrical subsystem 12 to float freely in the brain. This may be accomplished by the stylet being selectively flexible (through electrical stimulus or other suitable method) or by being resorbable into the tissue after a period of time. The stylet is preferably made from a stiff material such as metal, but may alternatively be made from any suitable material. In one variation, the metal is preferably insulated metal wire. In this variation, the insulated metal wire may not have insulation covering a sharpened tip, and thus can be used as a conventional single-channel microelectrode.

The preferred method of implanting the electrode lead system 10 includes any combination of the following steps (or any other suitable steps):

attaching the chamber 26 to the scull (preferably in a cranial burr-hole) of a patient;

implanting, through the guide tube 24 and/or with a stylet, a first electrode lead system with a guiding element and a series of first electrical subsystem 12 in a three-dimensional arrangement which are preferably mapping electrode systems;

removing, through the guide tube 24 and/or with a stylet, the first electrode lead system 10 following microelectrode recording;

implanting, through the guide tube and/or with a stylet, a second electrode lead system 10 with a series of guiding element and a series of first electrical subsystem 12 in a three-dimensional arrangement which are preferably neural interface electrode arrays coupled via a connector 14 to a second electrical subsystem;

removing the guide tube 24 over the second electrical subsystem and/or removing the stylet;

placing the second electrical subsystem within the chamber 26; and sealing the electrical subsystems within the chamber 26.

Although omitted for conciseness, the preferred embodiments include every combination and permutation of the various electrode lead systems, the various electrical subsystems, the various cables, and the various guide tubes.

As a person skilled in the art will recognize from the previous detailed description and from the figures and claims, modifications and changes can be made to the preferred embodiments of the invention without departing from the scope of this invention defined in the following claim.

We claim:

1. An electrode lead for implantation into body tissue, the lead comprising:
    a) a carrier comprising a rigid three-dimensional shape extending along a carrier length from a carrier proximal end to a carrier distal end;
    b) an electrode array comprising a plurality of electrodes supported on the carrier in the rigid three-dimensional shape; and
    c) a guiding element extending from a guiding element proximal end to a guiding element distal end, wherein the guiding element distal end is connected to the electrode array, and wherein the guiding element is configured to have a first three-dimensional shape, and
    d) wherein the guiding element is maneuverable into a second three-dimensional shape that is different than the first three-dimensional shape while the carrier supporting the plurality of electrodes connected to the distal end of the guiding element maintains its rigid three-dimensional shape, and
    e) wherein the plurality of electrodes comprise stimulation electrodes configured for electrical stimulation of biological tissue and recording electrodes configured for recording of biological activity from biological tissue and wherein there are at least a first row and a second row of four stimulation electrodes along the carrier length, the stimulation electrodes being equally spaced around a circumference of the carrier, and two diametrically opposed recording electrodes positioned between the first and second rows of stimulation electrodes.

2. The electrode lead of claim 1, wherein the electrode array is configured to be interfacable with neural tissue.

3. The electrode lead of claim 1 wherein the stimulation electrodes have a surface area of $0.196$ mm$^2$.

4. The electrode lead of claim 1 wherein the recording electrodes have a surface area of $0.00196$ mm$^2$.

5. The electrode lead of claim 1 wherein the electrode array is patterned on a thin-film polymer substrate, a silicon substrate, and combinations thereof.

6. The electrode lead of claim 1 further comprising at least one conductive interconnect extending from the electrode array to a bond pad configured for electrical connection to an external instrumentation.

7. The electrode lead of claim 1, wherein the guiding element proximal end is configured to be electrically connectable to an electrical subsystem.

8. The electrode lead system of claim 1 wherein the first and second rows of stimulation electrodes are spaced apart by $750$ μm along the carrier length.

9. The electrical lead of claim 1 wherein the guiding element supports at least one conductor electrically connected to the proximal end of the electrode array.

10. The electrical lead of claim 1 wherein the guiding element is electrically connected to the proximal end of the electrode array.

11. The electrical lead of claim 1 wherein there are sixty-four stimulation electrodes and thirty-two recording electrodes.

12. The electrical lead of claim 1 wherein individual electrodes of the electrode array are energizable in either a monopolar or a bipolar mode.

13. The electrical lead of claim 1 wherein the guiding element comprises a system of manipulatable cables.

14. The electrical lead of claim 1 wherein the guiding element comprises robotics that are controllable by a user.

15. The electrical lead of claim 1 wherein the guiding element comprises joints that are controllable by a user.

16. The electrical lead of claim 1 wherein the guiding element is of a shape memory material.

17. The electrical lead of claim 16 wherein the shape memory material is adapted to change shape upon either a change in temperature or electrical stimulation.

18. The electrical lead of claim 1 wherein the carrier has a pointed distal end.

19. An electrode lead for implantation into body tissue, the electrode lead comprising:
   a) a tubular carrier comprising a rigid three-dimensional shape extending along a carrier length from a carrier proximal end to a carrier distal end;
   b) an electrode array supported on the tubular carrier in the rigid three-dimensional shape, wherein the electrode array comprises sixty-four stimulation electrodes and thirty-two recording electrodes; and
   c) a guiding element extending from a guiding element proximal end to a guiding element distal end, wherein the guiding element distal end is electrically connected to the electrode array, and wherein the guiding element is configured to have a first three-dimensional shape, and;
   d) wherein the guiding element is maneuverable into a second three-dimensional shape that is different than the first three-dimensional shape while the carrier supporting the plurality of electrodes connected to the distal end of the guiding element maintains its rigid three-dimensional shape, and
   e) wherein the sixty-four stimulation electrodes are arranged in stimulation groups of four stimulation electrodes equally spaced annularly around a circumference of the carrier at sixteen spaced axial locations along the carrier length and wherein the thirty-two recording electrodes are arranged in recording groups of two recording electrodes positioned on opposites sides of the carrier between immediately adjacent annular stimulation electrode groups.

20. The electrode lead of claim 19, wherein the stimulation electrodes have a surface area of 0.196 mm$^2$.

21. The electrode lead of claim 19 wherein the recording electrode have a surface area of 0.00196 mm$^2$.

22. The electrode lead of claim 19 wherein the first and second rows of stimulation electrodes are spaced apart by 750 µm along the carrier length.

23. The electrode lead of claim 19, wherein the guiding element includes maneuverable joints.

24. The electrode lead of claim 19 including a guide tube that facilitates implantation of a plurality of the electrode leads into body tissue.

25. The electrical lead of claim 19 wherein the guiding element supports at least one conductor electrically connected to the proximal end of the electrode array.

26. The electrical lead of claim 19 wherein the guiding element is electrically connected to the proximal end of the electrode array.

27. An electrode lead system for implantation into body tissue, the lead system comprising:
   a) a plurality of leads, each lead comprising:
      i) a carrier comprising a rigid three-dimensional shape extending along a carrier length from a carrier proximal end to a carrier distal end;
      ii) an electrode array comprising a plurality of electrodes distributed along the carrier in the three-dimensional shape, wherein the plurality of electrodes comprise stimulation electrodes configured for electrical stimulation of biological tissue and recording electrodes configured for recording of biological activity from biological tissue and wherein there are at least a first row and a second row of four stimulation electrodes along the carrier length, the stimulation electrodes being equally spaced around a circumference of the carrier, and two diametrically opposed recording electrodes positioned between the first and second rows of stimulation electrodes; and
      iii) a guiding element extending from a guiding element proximal end to a guiding element distal end, wherein the guiding element distal end is connected to the electrode array, and wherein the guiding element is configured to have a first three-dimensional shape, and
      iv) wherein the guiding element is maneuverable into a second three-dimensional shape that is different than the first three-dimensional shape while the carrier supporting the plurality of electrodes connected to the distal end of the guiding element maintains its rigid three-dimensional shape;
   b) an electrical subsystem; and
   c) at least one interconnect that couples the electrode array to the electrical subsystem.

28. The electrode lead system of claim 27 further comprising a guide tube that facilitates implantation of the lead into body tissue.

29. The electrode lead system of claim 28 wherein when housed inside the guide tube, the electrical lead extends substantially along a longitudinal axis of the guide tube.

30. The electrode lead system of claim 27 wherein the connector is a flexible ribbon cable.

31. The electrical lead of claim 27 wherein the stimulation electrodes have a surface area of 0.196 mm$^2$.

32. The electrical lead of claim 27 wherein the recording electrodes have a surface area of 0.00196 mm$^2$.

33. The electrical lead system of claim 27 wherein the guiding element supports at least one conductor electrically connected to the proximal end of the electrode array.

34. The electrical lead system of claim 27 wherein the guiding element is electrically connected to the proximal end of the electrode array.

35. The electrical lead system of claim 27 wherein the interconnect comprises a flexible ribbon cable.

36. The electrical lead of claim 35 wherein the ribbon cable is encased in silicone.

37. The electrical lead system of claim 27 wherein the interconnect comprises fluidic channels.

38. An electrode lead for implantation into body tissue, the lead comprising:
   a) a first electrical subsystem comprising a three-dimensional shape extending from a distal end to a proximal end, wherein the first electrical subsystem includes a plurality of electrodes that are configured for either electrical stimulation of biological tissue or recordation of biological activity;

b) a guiding element configured to have a first three-dimensional shape extending from a guiding element distal end to a guiding element proximal end, wherein the guiding element distal end is connected to the first electrical subsystem proximal end and wherein the guiding element proximal end is configured to be electrically connectable to a second electrical subsystem; and c) wherein the guiding element is maneuverable into a second three-dimensional shape that is different than the first three-dimensional shape while the first electrical subsystem comprising the plurality of electrodes connected to the distal end of the guiding element maintains its rigid three-dimensional shape, and d) wherein there are at least a first row and a second row of four stimulation electrodes along the carrier length, the stimulation electrodes being equally spaced around a circumference of the carrier, and two diametrically opposed recording electrodes positioned between the first and second rows of stimulation electrodes.

39. The electrical lead of claim 38 wherein the guiding element supports at least one conductor electrically connected to the proximal end of the electrode array.

40. The electrical lead of claim 38 wherein the guiding element is electrically connected to the proximal end of the electrode array.

41. An electrode lead for implantation into body tissue, the lead comprising:

a) a cylindrical carrier extending along a carrier length from a carrier proximal end to a carrier distal end;

b) an electrode array comprising a plurality of electrodes supported on the carrier in a rigid three-dimensional shape; and c) a guiding element extending from a guiding element proximal end to a guiding element distal end, wherein the guiding element distal end is connected to the electrode array, and wherein the guiding element is configured to have a first three-dimensional shape, and d) wherein the guiding element is maneuverable into a second three-dimensional shape that is different than the first three-dimensional shape while the carrier supporting the plurality of electrodes connected to the distal end of the guiding element maintains its cylindrical three-dimensional shape, and e) wherein the plurality of electrodes comprise stimulation electrodes configured for electrical stimulation of biological tissue and recording electrodes configured for recording of biological activity from biological tissue and wherein there are at least a first row and a second row of four stimulation electrodes along the carrier length, the stimulation electrodes being equally spaced around a circumference of the carrier, and two diametrically opposed recording electrodes positioned between the first and second rows of stimulation electrodes.

* * * * *